US009669395B2

(12) United States Patent
Hung et al.

(10) Patent No.: US 9,669,395 B2
(45) Date of Patent: Jun. 6, 2017

(54) CATALYST COMPOSITION FOR PREPARING O-PHENYLPHENOL AND METHOD FOR PREPARING O-PHENYLPHENOL WITH THE CATALYST COMPOSITION

(71) Applicant: China Petrochemical Development Corporation, Taipei (TW)

(72) Inventors: Wei-Ying Hung, Taipei (TW); Chia-Hui Shen, Taipei (TW); Zih-Hua Li, Taipei (TW)

(73) Assignee: China Petrochemical Development Corporation, Taipei (TW)

(*) Notice: Subject to any disclaimer, the term of this patent is extended or adjusted under 35 U.S.C. 154(b) by 0 days.

(21) Appl. No.: 15/148,270

(22) Filed: May 6, 2016

(65) Prior Publication Data
US 2016/0326077 A1 Nov. 10, 2016

(30) Foreign Application Priority Data
May 7, 2015 (TW) .............................. 104114546 A

(51) Int. Cl.
B01J 23/64 (2006.01)
B01J 23/58 (2006.01)
B01J 23/652 (2006.01)
C07C 37/07 (2006.01)
B01J 27/25 (2006.01)
B01J 21/04 (2006.01)
B01J 23/46 (2006.01)
B01J 23/89 (2006.01)
B01J 23/04 (2006.01)
B01J 27/055 (2006.01)
B01J 27/232 (2006.01)
C07C 45/74 (2006.01)

(52) U.S. Cl.
CPC ............... *B01J 27/25* (2013.01); *B01J 21/04* (2013.01); *B01J 23/04* (2013.01); *B01J 23/462* (2013.01); *B01J 23/468* (2013.01); *B01J 23/58* (2013.01); *B01J 23/6522* (2013.01); *B01J 23/892* (2013.01); *B01J 27/055* (2013.01); *B01J 27/232* (2013.01); *C07C 37/07* (2013.01); *C07C 45/74* (2013.01); *B01J 23/64* (2013.01)

(58) Field of Classification Search
None
See application file for complete search history.

(56) References Cited

U.S. PATENT DOCUMENTS 3,534,110 A * 10/1970 Le Page .................. C07C 37/06 502/243
3,580,970 A * 5/1971 Swift ....................... B01J 21/08 502/242
3,932,536 A 1/1976 Weissel et al.
4,060,559 A * 11/1977 Goto ....................... C07C 37/06 502/237

FOREIGN PATENT DOCUMENTS

| CN | 1371897 A | 10/2002 |
| JP | 51-149248 | * 12/1976 |
| TW | 201226379 A | 7/2012 |
| TW | 201334868 A | 9/2013 |
| TW | I460156 B | 11/2014 |

OTHER PUBLICATIONS

Juichi, I. et al. Patent No. JP51-149248; Published Dec. 22, 1976; pp. 1-6; English translation.*
Kumar, V. P. et al. "Noble Metal Promoted CeO2—ZrO2-Supported Ni Catalysts for Liquid-Phase Hydrogenation of Cinnamaldehyde" Catal. Lett. (2013) 143:1266-1276.*
Taiwanese Office Action issued in corresponding Application No. TW 104114546, Feb. 19, 2016, 6 pages.

* cited by examiner

*Primary Examiner* — Medhanit Bahta
(74) *Attorney, Agent, or Firm* — Mintz Levin Cohn Ferris Glovsky and Popeo, P.C.; Peter F. Corless; Richard B. Emmons

(57) ABSTRACT

A catalyst composition for preparing o-phenylphenol is provided. The catalyst composition includes a carrier; and a first active metal, a second active metal, and a catalytic promoter carried by the carrier. The first active metal is platinum, and the second active metal is selected from the first, second and third rows of transition metals of groups VIB and VIIIB. The present disclosure utilizes the carrier to carry the first active metal, the second active metal and the catalytic promoter so as to increase the selectivity of o-phenylphenol and the service life of a catalyst.

15 Claims, No Drawings

CATALYST COMPOSITION FOR PREPARING O-PHENYLPHENOL AND METHOD FOR PREPARING O-PHENYLPHENOL WITH THE CATALYST COMPOSITION

CROSS-REFERENCES TO RELATED APPLICATIONS

This application claims under 35 U.S.C. §119(a) the benefit of Taiwanese Application No. 104114546, filed May 7, 2015, the entire contents of which are incorporated herein by reference.

BACKGROUND

1. Technical Field

The present disclosure relates to a catalyst composition, and more particularly, to a catalyst composition for preparing ortho-phenylphenol (OPP).

2. Description of Related Art

OPP is a chemical product having a wide range of applications. In addition to being used as a preservative for fruits and vegetables, OPP also can be used for the synthesis of 9,10-dihydro-9-oxa-10-phosphaphenanthrene-10-oxide (DOPO) as an intermediate of a phosphorus-based flame retardant, the synthesis of sodium ortho-phenylphenol (SOPP) as a preservative, a bactericide or a dyeing carrier, and the synthesis of ortho-phenyl phenoxy ethyl acrylate (OPPEA) as an optical material. Further, OPP can be used in other fields, such as the fields of heat stabilizers and surfactants.

There are many methods for synthesizing OPP, which can mainly be categorized into methods of either separation or synthesis. Methods of separation each includes steps of producing phenol by sulfonation of chlorobenzene, and separating and purifying the distillation residue to obtain OPP. However, with the gradual change in the method for producing phenol, such separation method is inappropriate at present due to the stringent reaction conditions and the limited yield.

Therefore, the synthesis methods are commonly used for producing OPP, and they can be further categorized into methods of sulfonation (halogenation) and hydrolysis of phenylbenzene, methods of coupling of chlorobenzene and phenol, and the like, based on the raw materials used. Currently, in terms of availability and cost consideration, cyclohexanone is widely used as a raw material in industry. In such process, cyclohexanone is first condensed to produce a dimer (2-(1-cyclohexenyl) cyclohexanone or 2-cyclohexylidene cyclohexanone). Subsequently, a dehydrogenation reaction of such dimer is performed, and thereby obtaining the product OPP. This reaction is shown by the following formula (I):

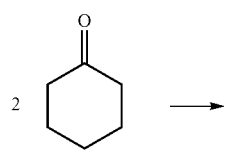

(I)

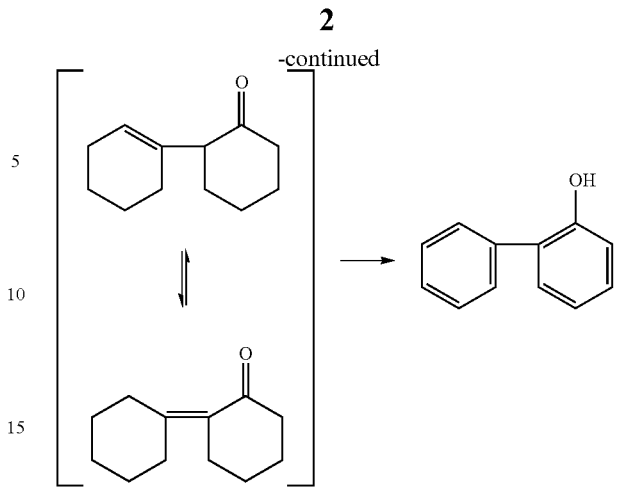

In the reaction for preparing OPP from the cyclohexanone dimer, the catalysts used can be broadly categorized into metal alloy catalysts, supported non-noble metal catalysts, and supported noble metal catalysts. Among these, as compared to the other kinds, the metal alloy catalysts are prone to cementation during the reaction, and its selectivity of the product OPP is lower, as well as stability is poorer. Moreover, the process for synthesizing a metal alloy catalyst is more complicated. For example, as shown in U.S. Pat. No. 3,932,536A, which employs a nickel-copper-aluminum-chromium alloy catalyst, the selectivity of OPP was initially 81%, and reduced to 70% after 1,000 hours of reaction.

Further, aluminum oxide, activated carbon, silicon dioxide or other metal oxides, as a single molecule or a complex, is commonly used as a carrier for the supported catalyst. A non-noble metal catalyst does not contain a noble metal as an active component, such that it is conductive to effective cost reduction. However, even though the conversion rate and the yield are not changed after such supported non-noble metal catalyst is reacted for 300 hours, the catalytic activity and the reactivity of the supported non-noble metal catalyst are still unable to meet the standard of industrial production.

It is obvious that such metal alloy catalyst and supported non-noble metal catalyst have disadvantages of the insufficient service life of the catalyst, the catalytic activity, and reactivity for industrial production.

Platinum and palladium are often used as active components for a noble metal catalyst. Such kind of catalyst is first applied in the production of OPP. For example, in CN1371897A, which employs a molecular sieve catalyst containing palladium, even though the conversion rate of a dimer was initially 98% and the selectivity of OPP was initially 100%, the conversion rate of the dimer was reduced to 92% and the selectivity of OPP was reduced to 97% after 200 hours of reaction.

In addition, for increasing the catalytic activity, other catalytic promoters are added for modifying a catalyst. As shown in Journal of China University of Petroleum (Edition of Natural Science), 2012, 36(3):165-174, it is found that, by using a catalyst in which platinum is carried by aluminum oxide and adding an appropriate amount of potassium carbonate as a catalytic promoter at an appropriate time, the selectivity could be effectively increased to 94%. However, as shown in Chemical Industry and Engineering Progress, 2004, 23(1):59-61, which relates to the use of γ-aluminum oxide carrying 0.3% by weight of platinum thereon and the addition of potassium sulfate as a catalytic promoter, even though the conversion rate of a dimer was initially 98.7% and the selectivity of OPP was initially 96.8%, the conversion rate was reduced to 88.1% and the yield of OPP was reduced to 84% after 50 hours of reaction; and the conversion rate as reduced to 88.1% and the yield of OPP was reduced to below 80% after 100 hours of reaction. Moreover, as shown in JP51-149248, which employs a catalyst in which platinum, iridium (group VIIIB) and an alkali metal hydroxide are carried by a carrier, wherein the amount of platinum is 0.1 to 5.0% by weight, the weight ratio of iridium to platinum is 0.1 to 0.4, the amount of alkali metal hydroxide is 0.5 to 8.0% by weight, and the carrier is an aluminum oxide-silicon dioxide complex carrier containing up to 0.1% iron or 90% by weight of aluminum oxide (based on the total weight of ferric oxide in the carrier). However, in such catalyst, the conversion rate of a dimer was only 92%, and the selectivity of OPP was 93%.

Besides, CN101524643 employs aluminum oxide as a carrier, platinum as an active metal, and citric acid as a competitive adsorbent, and adds sodium sulfate as a catalytic promoter for preparing a catalyst. Even though the conversion rate was initially 100% and the selectivity was initially 95%, the conversion rate was reduced to 99.8% after 2,000 hours of reaction.

From the above, although the supported noble metal catalyst exhibits higher conversion rate and selectivity, its service life is insufficient to withstand a long period of reaction. As a result, the catalytic activity cannot be effectively maintained, and the stability of the catalyst is poor.

Therefore, the most urgent problem to be solved is to increase the overall stability and the service life of catalyst.

SUMMARY

In order to resolve the above-mentioned drawbacks, the present disclosure provides a catalyst composition for preparing OPP, including: a carrier; and a first active metal, a second active metal and a catalytic promoter carried by the carrier, wherein the first active metal is platinum, the second active metal is selected from the first, second and third rows of transition metals of groups VIB and VIIIB, and the catalytic promoter is selected from the group consisting of a metal salt and a metal hydroxide.

The present disclosure further provides a method for preparing OPP, including: performing a dehydrogenation reaction of a cyclohexanone dimer in the presence of the catalyst composition of the present disclosure.

In one embodiment of the catalyst composition and the method of the present disclosure, the weight ratio of the second active metal to the first active metal is between 0.03 and 0.38. In another embodiment, the weight ratio of the second active metal to the first active metal is between 0.08 and 0.3.

In one embodiment of the catalyst composition and the method of the present disclosure, the weight ratio of the first active metal to the carrier is between 0.004 and 0.006.

In the above embodiment, the weight ratio of the second active metal to the carrier is between 0.0002 and 0.0015. In another embodiment, the weight ratio of the second active metal to the carrier is between 0.0005 and 0.0012.

In one embodiment of the catalyst composition and the method of the present disclosure, the second active metal is selected from the group consisting of chromium, ruthenium, iridium and nickel.

In one embodiment of the catalyst composition and the method of the present disclosure, the metal salt is alkali metal sulfate, alkali metal carbonate or alkali metal nitrate. The examples of the catalytic promoter can be at least one selected from the group consisting of potassium sulfate, potassium carbonate, and sodium nitrate.

In one embodiment of the catalyst composition and the method of the present disclosure, the metal hydroxide is alkali metal hydroxide. An example of the catalytic promoter can be potassium hydroxide.

In one embodiment of the catalyst composition and the method of the present disclosure, the weight ratio of the catalytic promoter to the carrier is between 0.02 and 0.15.

In one embodiment of the catalyst composition and the method of the present disclosure, the carrier is at least one selected from the group consisting of $SiO_2$, $Al_2O_3$, and $Zr_2O_3$.

In one embodiment of the method of the present disclosure, the weight hourly space velocity (WHSV) in the dehydrogenation reaction is between 0.2 and 2.0.

The present disclosure utilizes the catalyst composition, in which the carrier that carries platinum as the first active metal further carries the second active metal selected from the first, second and third rows of transition metals of groups VIB and VIIIB, so as to increase the dispersity of platinum. The carrier also carries the catalytic promoter, so as to maintain the conversion rate of the cyclohexanone dimer at 99.97% to 100% during the preparation of OPP, thereby effectively increasing the service life of the catalyst. Accordingly, the catalyst composition of the present disclosure is useful for industrial production.

It can be seen from the above that the catalyst composition of the present disclosure utilizes the carrier to carry platinum, a metal selected from the first, second and third rows of transition metals of groups VIB and VIIIB, and a catalytic promoter, so as to obtain not only a high conversion rate of a cyclohexanone dimer, but also high selectivity of OPP, while maintaining the conversion rate of the cyclohexanone dimer after a long period of reaction.

Further, the catalyst composition of the present disclosure has a longer service life of the catalyst, and it is suitable for different reaction temperatures and has a broader range of the WHSV of a reactant. Therefore, the catalyst composition of the present disclosure can satisfy different demands in the industrial process.

DETAILED DESCRIPTION

The detailed description of the present disclosure is illustrated by the following specific examples. Persons skilled in the art can conceive the other advantages and effects of the present disclosure, based on the disclosure contained in the present specification. The present disclosure can also be implemented or applied by different embodiments. Each of the details in the present specification can be modified and altered in various ways, based on different perspectives and applications, without departing from the spirit of the disclosure of the present disclosure.

As used herein, the expression "first, second and third rows in groups VIB and VIIIB" refers to the first row, second row transition, and third row in groups VIB and VIIIB in the periodic table.

The conversion rate and selectivity described herein are calculated by the following formulas:

Conversion rate (%)={[addition amount of a cyclohexanone dimer (mol)−residual amount of the cyclohexanone dimer after reaction (mol)]/addition amount of cyclohexanone dimer (mol)}×100%;

Selectivity (%)={amount of OPP in a product (mol)/[addition amount of the cyclohexanone dimer (mol)−residual amount of the cyclohexanone dimer after reaction (mol)]}×100%; and Reaction initiation=6 hours after the reaction starts.

In addition, the weight ratio of the first active metal:the second active metal:the carrier:the catalytic promoter in the catalyst composition is measured by Varian 220FS Atomic absorption spectrometer, AAS), wherein the loading rate of the first active metal, the second active metal, and the catalytic promoter on the carrier are all greater than 92%.

The present disclosure provides a catalyst composition for preparing OPP from a cyclohexanone dimer, and the catalyst composition includes a carrier; and a first active metal, a second active metal, and a promoter selected from a metal salt and a metal hydroxide carried by the carrier.

In addition, for preparing the catalyst composition, platinum is used as the first active metal, a metal selected from the first, second and third rows of transition metals of groups VIB and VIIIB is used as the second active metal. The first active metal and the second active metal are carried by the carrier, such as, $SiO_2$, $Al_2O_3$ and $Zr_2O_3$. Subsequently, in a solution environment, the catalyst promoter selected from a metal salt and a metal hydroxide is carried by the carrier, such that the catalyst composition is represented by the following formula (II):

[Pt+M+catalytic promoter]/γ-$Al_2O_3$ (II)

wherein M is selected from the first, second and third rows of transition metals of groups VIB and VIIIB In one embodiment, platinum and the transition metals of groups VIB and VIIIB are carried by γ-aluminum oxide. After the γ-aluminum oxide is subjected to dehydration and calcination, in a solution environment, the catalytic promoter selected from a metal salt and a metal hydroxide is carried by the carrier. The obtained catalyst can be used for preparing OPP.

In the catalyst composition of the present disclosure, the weight ratio of platinum as the first active metal to the carrier is between 0.004 and 0.006. The weight ratio of the second active metal selected from the first, second and third rows of transition metals of groups VIB and VIIIB to the carrier is between 0.0002 and 0.0015, preferably between 0.0005 and 0.0012. The weight ratio of the catalytic promoter to the carrier is between 0.02 and 0.15, preferably between 0.05 and 0.10.

The present disclosure further provides a method for preparing OPP, including: performing a dehydrogenation reaction of a cyclohexanone dimer in the presence of the catalyst composition of the present disclosure.

In one embodiment of the method for preparing OPP of the present disclosure, the weight ratio of the second active metal to the first active metal is between 0.03 and 0.38. In another embodiment, the weight ratio of the second active metal to the first active metal is between 0.08 and 0.3.

In one embodiment of the method for preparing OPP of the present disclosure, the weight ratio of the first active metal to the carrier is between 0.004 and 0.006.

In the above embodiments, the weight ratio of the second active metal to the carrier is between 0.0002 and 0.0015. In another embodiment, the weight ratio of the second active metal to the carrier is between 0.0005 and 0.0012.

In one embodiment of the method for preparing OPP of the present disclosure, the second active metal is selected from the group consisting of chromium, ruthenium, iridium and nickel.

In one embodiment of the method for preparing OPP of the present disclosure, the metal salt is alkali metal sulfate, alkali metal carbonate, or alkali metal nitrate. The examples of the catalytic promoter can be selected from at least one from the group consisting of potassium sulfate, potassium carbonate, and sodium nitrate.

In one embodiment of the method for preparing OPP of the present disclosure, the metal hydroxide is an alkali metal hydroxide. The examples of the catalytic promoter can be potassium hydroxide.

In one embodiment of the method for preparing OPP of the present disclosure, the weight ratio of the catalytic promoter to the carrier is between 0.02 and 0.15.

In one embodiment of the method for preparing OPP of the present disclosure, the carrier is selected from at least one from the group consisting of $SiO_2$, $Al_2O_3$, and $Zr_2O_3$.

In one embodiment of the method for preparing OPP of the present disclosure, the WHSV in the dehydrogenation reaction is between 0.2 and 2.0.

Preparation Example 1: Preparation of a Catalyst Composition of the Present Disclosure 1.335 g of hexachloroplatinic acid and 0.619 g of chromium (III) nitrate nonahydrate were dissolved in 300 g of deionized water. 100 g of γ-aluminum oxide calcinated for 3 hours at 250° C. was added into the above solution of metal salts. The solution was impregnated until dried out by ultrasonication at 70° C., oven-dried, and dehydrated. After then, the solution was calcinated for 5 hours at 450° C. in the presence of nitrogen gas at a flow rate of 30 standard-state cubic centimeter per minute (sccm), followed by a reduction reaction for 5 hours at 360° C. in the presence of nitrogen gas at a flow rate of 30 sccm, and hydrogen gas at a flow rate of 10 sccm, A catalyst without a supported catalytic promoter was obtained.

6.316 g of potassium sulfate was dissolved in 300 g of deionized water, and then the reduced catalyst was added into the aqueous solution of potassium sulfate. The solution was impregnated until dried out by ultrasonication at 70° C., oven-dried, and dehydrated. The catalyst composition of Preparation Example 1 was obtained, wherein the weight ratio of first active metal:second active metal:carrier:catalytic promoter was 0.5:0.08:100:6.

Preparation Examples 2 to 4: Preparation of Catalyst Compositions of the Present Disclosure by Using Different Second Active Metals These catalyst compositions were prepared in the same manner as in Preparation Example 1, except that 0.619 g of chromium (III) nitrate nonahydrate in Preparation Example 1 was replaced by 0.208 g of ruthenium (III) chloride trihydrate, 0.153 g of iridium (III) chloride hydrate, and 0.326 g of nickel (II) chloride hexahydrate in Preparation Examples 2 to 4, respectively. The weight ratio of first active metal:second active metal:carrier:catalytic promoter in Preparation Examples 2 to 4 was 0.5:0.08:100:6.

Preparation Examples 5 to 8: Preparation of Catalyst Compositions of the Present Disclosure by Using Second Active Metals in Different Amounts These catalyst compositions were prepared in the same manner as in Preparation Example 1, except that the addition amounts of chromium (III) nitrate nonahydrate in Preparation Examples 5 to 8 were 0.155 g, 0.388 g, 0.930 g and 1.161 g, respectively. Accordingly, the weight ratios of first active metal:second active metal:carrier:catalytic promoter in the catalyst compositions of Preparation Examples 5 to 8 became 0.5:0.02:100:6, 0.5:0.05:100:6, 0.5:0.12:100:6, 0.5:0.15:100:6, respectively.

Preparation Examples 9 to 11: Preparation of Catalyst Compositions of the Present Disclosure by Using Different Catalytic Promoters These catalyst compositions were prepared in the same manner as in Preparation Example 1, except that potassium sulfate in Preparation Example 1 was replaced by potassium carbonate, potassium hydroxide, and sodium nitrate in Preparation Examples 9 to 11, respectively. In Preparation Examples 9 to 11, the weight ratio of first active metal:second active metal:carrier:catalytic promoter was 0.5:0.08:100:6.

Preparation Examples 12 to 15: Preparation of Catalyst Compositions of the Present Disclosure by Using Catalytic Promoters in Different Amounts These catalyst compositions were prepared in the same manner as in Preparation Example 1, except that the addition amount (6.316 g) of potassium sulfate in Preparation Example 1 was adjusted to 2.105 g, 8.421 g, 11.579 g and 15.789 g in Preparation Examples 12 to 15, respectively. Accordingly, the weight ratios of first active metal:second active metal:carrier:catalytic promoter in the catalyst compositions of Preparation Examples 12 to 15 became 0.5:0.08:100:2, 0.5:0.08:100:8, 0.5:0.08:100:11, 0.5:0.08:100:15, respectively.

Comparative Example 1: Preparation of a Catalyst Composition without Using a Second Active Metal and Preparation of OPP 1.335 g of hexachloroplatinic acid was dissolved in 300 g of deionized water, and then 100 g of γ-aluminum oxide calcinated for 3 hours at 250° C. was added into the above solution of metal salts. The solution was impregnated until dried out by ultrasonication at 70° C., oven-dried, and dehydrated. After then, the solution was calcinated for 5 hours at 450° C. in the presence of nitrogen gas at a flow rate of 30 sccm, followed by a reduction reaction for 5 hours at 360° C. in the presence of nitrogen gas at a flow rate of 30 sccm, and hydrogen gas at a flow rate of 10 sccm. Subsequently, 6.316 g of potassium sulfate was dissolved in 300 g of deionized water, and then the reduced catalyst was added into the solution. The solution was then impregnated until dried out by ultrasonication at 70° C., oven-dried, and dehydrated.

20 g of the obtained catalyst composition was filled in a fixed-bed reactor. The reaction was carried out in a continuous mode. A cyclohexanone dimer was fed into the reactor at a flow rate of 0.33 sccm, and hydrogen gas was also fed into the reactor as a carrier gas. The dehydrogenation reaction of the cyclohexanone dimer was performed at a vaporization temperature of 240° C., a reaction temperature of 360° C., and a reaction pressure of 1 atm. The product was collected after the reaction was performed for 6 hours, and it was analyzed by Shimadzu GC-2010 Plus gas chromatography. The result of the analysis is reported in Table 1.

Examples 1 to 15: Methods for Preparing OPP of the Present Disclosure 20 g of the catalyst compositions prepared from Preparation Examples 1 to 15 were filled in a fixed-bed reactor, respectively. The reaction was carried out in the continuous mode. A cyclohexanone dimer was fed into the reactor at a flow rate of 0.33 sccm, and hydrogen gas was also fed into the reactor as a carrier gas. The dehydrogenation reaction of cyclohexanone dimer was performed at a vaporization temperature of 240° C., a reaction temperature of 360° C., and a reaction pressure of 1 atm. The products were collected after the reaction was performed for 6 hours, and they were analyzed by Shimadzu GC-2010 Plus gas chromatography. The results of the analysis are reported in Tables 1 to 4.

TABLE 1

|  | Catalyst composition | Second active metal | Conversion rate (%) | Selectivity (%) |
| --- | --- | --- | --- | --- |
| Comparative Example 1 | — | — | 99.98 | 87.45 |
| Example 1 | Preparation Example 1 | chromium | 100.00 | 92.44 |
| Example 2 | Preparation Example 2 | ruthenium | 100.00 | 91.48 |
| Example 3 | Preparation Example 3 | iridium | 100.00 | 90.13 |
| Example 4 | Preparation Example 4 | nickel | 100.00 | 91.06 |

Referring to Table 1, as compared with the catalyst of Comparative Example 1, the catalyst composition of the present disclosure had an excellent property of the conversion rate of the cyclohexanone dimer being 100% after 6 hours of reaction, due to that the carrier in the catalyst composition of the present disclosure carried the first and second active metals. Further, the catalyst composition of the present disclosure resulted in a selectivity greater than 90% under the condition of a conversion rate of 100%.

TABLE 2

|  | Catalyst composition | Weight ratio of second active metal in catalyst composition | Conversion rate (%) | Selectivity (%) |
| --- | --- | --- | --- | --- |
| Example 5 | Preparation Example 5 | 0.02 | 100.00 | 88.23 |
| Example 6 | Preparation Example 6 | 0.05 | 100.00 | 89.25 |
| Example 1 | Preparation Example 1 | 0.08 | 100.00 | 92.44 |
| Example 7 | Preparation Example 7 | 0.12 | 100.00 | 89.31 |
| Example 8 | Preparation Example 8 | 0.15 | 100.00 | 93.74 |

In the catalyst compositions from Preparation Examples 1, 5 to 8, the weight ratio of first active metal:carrier:catalytic promoter was fixed at 0.5:100:6, and the amount of second active metal was changed. The weight ratios of the second active metal in each Preparation Example are shown in Table 2.

Referring to Table 2, as compared with Comparative Example 1 (see Table 1), when the weight ratio of the second active metal to the carrier in the catalyst composition of the present disclosure was between 0.0002 and 0.0015, not only that the conversion rate of the reactant was not be decreased, but also that the selectivity of the product could be maintained under the condition of a conversion rate of the reactant of 100%.

Comparative Example 2: Preparation of a Catalyst Composition without a Catalytic Promoter 1.335 g of hexachloroplatinic acid and 0.619 g of chromium (III) nitrate nonahydrate were dissolved in 300 g of deionized water. 100 g of γ-aluminum oxide calcinated for 3 hours at 250° C. was added into the above solution of metal salts. the solution was then impregnated until dried out by ultrasonication at 70° C., oven-dried, and dehydrated. After then, the catalyst was calcinated for 5 hours at 450° C. in the presence of nitrogen gas at a flow rate of 30 sccm, followed by a reduction reaction for 5 hours at 360° C. in the presence of nitrogen gas at a flow rate of 30 sccm and hydrogen gas at a flow rate of 10 sccm.

20 g of the obtained catalyst composition was filled in a fixed-bed reactor. The reaction was carried out in a continuous mode. A cyclohexanone dimer was fed into the reactor at a flow rate of 0.33 sccm, and hydrogen gas was also fed into the reactor as a carrier gas. The dehydrogenation reaction of cyclohexanone dimer was performed at a vaporization temperature of 240° C., a reaction temperature of 360° C., and a reaction pressure of 1 atm. The product was collected after the reaction was performed for 6 hours, and analyzed by Shimadzu GC-2010 Plus gas chromatography. The result of the analysis is reported in Table 3.

TABLE 3

| | Catalyst composition | Catalytic Promoter | Conversion rate (%) | Selectivity (%) |
|---|---|---|---|---|
| Comparative Example 2 | — | | 100.00 | 71.26 |
| Example 1 | Preparation Example 1 | $K_2SO_4$ | 100.00 | 92.44 |
| Example 9 | Preparation Example 9 | $K_2CO_3$ | 100.00 | 85.60 |
| Example 10 | Preparation Example 10 | KOH | 100.00 | 84.72 |
| Example 11 | Preparation Example 11 | $NaNO_3$ | 99.97 | 80.12 |

In the catalyst compositions from Preparation Examples 1, 9 to 11, the weight ratio of first active metal:carrier:catalytic promoter was fixed at 0.5:0.08:100:6, and the amount of catalytic promoter was changed. The catalytic promoters in each of the Preparation Examples are shown in Table 3.

Referring to Table 3, the selectivity of the catalyst composition of Comparative Example 2 without a catalytic promoter was already lower than 80% within 6 hours of reaction time, i.e., reaction initiation. Unlike Comparative Example 2, all of the catalyst compositions from each of the Examples of the present disclosure (in which the different catalytic promoters) were used have a conversion rate of the reactant of greater than 99.97%, and their catalytic activities are maintained.

In addition, from Table 3, it can be seen that, as compared with Examples 10 and 11, when the catalytic promoter is alkali metal sulfate or alkali metal carbonate (for example, Examples 1 and 9), the catalyst composition of the present disclosure achieves a selectivity of the product of greater than 85.5% under the condition of a conversion rate of the product of 100%.

TABLE 4

| | Catalyst composition | Weight ratio of catalytic promoter in catalyst composition | Conversion rate (%) | Selectivity (%) |
|---|---|---|---|---|
| Example 12 | Preparation Example 12 | 2 | 100.00 | 81.17 |
| Example 1 | Preparation Example 1 | 6 | 100.00 | 92.44 |
| Example 13 | Preparation Example 13 | 8 | 100.00 | 94.09 |
| Example 14 | Preparation Example 14 | 11 | 100.00 | 89.97 |
| Example 15 | Preparation Example 15 | 15 | 100.00 | 89.99 |

In the catalyst compositions from Preparation Examples 1, 12 to 15, the weight ratio of first active metal:second active metal:carrier was fixed at 0.5:0.08:100, and the weight ratios of catalytic promoter were changed to be 2, 6, 8, 11 and 15, respectively. The catalytic promoters in each of the Preparation Examples are shown in Table 4.

As shown in Table 4, as compared with Comparative Example 2 (see Table 3), when the weight ratio of the catalytic promoter to the carrier in the catalyst composition of the present disclosure was between 0.02 to 0.15, the conversion rate of the reactant was not be decreased, and the selectivity of the product could be maintained under the condition of a conversion degree of the reactant of 100%.

Examples 16 to 20: Methods for Preparing OPP of the Present Disclosure 20 g of the catalyst composition prepared from Preparation Example 1 was filled in a fixed-bed reactor. The reaction was carried out in the continuous mode. A cyclohexanone dimer was fed into the reactor at a flow rate of 0.33 sccm, and a hydrogen was also fed into the reactor as a carrier gas. The dehydrogenation reaction of cyclohexanone dimer was performed at a vaporization temperature of 240° C., a reaction pressure of 1 atm, and different reaction temperatures. The reaction temperatures in each of the Examples are shown in Table 5. The products were collected after the reaction was performed for 6 hours, and analyzed by Shimadzu GC-2010 Plus gas chromatography. The results of the analysis are reported in Table 5.

TABLE 5

| | Reaction temperature (° C.) | Conversion rate (%) | Selectivity (%) |
|---|---|---|---|
| Example 16 | 330 | 100.00 | 92.16 |
| Example 17 | 345 | 100.00 | 91.25 |
| Example 1 | 360 | 100.00 | 91.89 |
| Example 18 | 370 | 100.00 | 91.58 |
| Example 19 | 380 | 100.00 | 92.00 |
| Example 20 | 400 | 100.00 | 91.34 |

As shown in Table 5, when OPP was prepared by using the catalyst composition of the present disclosure, the suitable reaction temperature was 330 to 400° C., and high selectivity as well as a high conversion rate could be obtained. Also, within a broader range of reaction temperatures, the method of the present disclosure could result in a high conversion rate of the reactant. Meanwhile, the selectivity of the product could be maintained under the condition of a conversion degree of the reactant of 100%, and the excellent catalytic activity could be maintained under the conditions of different reaction temperatures.

It can be seen that, in the method for preparing OPP of the present disclosure, the range of reaction temperature in the dehydrogenation reaction of cyclohexanone dimer was between 330 and 400° C.

Examples 21 to 27: Methods for Preparing OPP of the Present Disclosure 20 g of the catalyst composition prepared from Preparation Example 1 was filled in a fixed-bed reactor. The reaction was carried out in the continuous mode. A cyclohexanone dimer was fed into the reactor with different flow rates by standard-state cubic centimeter per minute (sccm), and hydrogen gas was also fed into the reactor as a carrier gas. The dehydrogenation reaction of cyclohexanone dimer was performed at a vaporization temperature of 240° C., a reaction temperature of 360° C., and a reaction pressure of 1 atm. More specifically, the flow rates in Examples 21 to 27 were 0.10 sccm, 0.20 sccm, 0.26 sccm, 0.40 sccm, 0.46 sccm, 0.56 sccm, and 0.66 sccm, respectively; and they can be converted into weight hourly space velocities (Weight Hourly Space Velocity, WHSV) of 0.3 $h^{-1}$, 0.6 $h^{-1}$, 0.8 $h^{-1}$, 1.2 $h^{-1}$, 1.4 $h^{-1}$, 1.7 $h^{-1}$, and 2.0 $h^{-1}$, respectively. The flow rates for feeding the cyclohexanone dimer in each of Examples are reported in Table 6. The products were collected after the reaction was performed for 6 hours, and they were analyzed by Shimadzu GC-2010 Plus gas chromatography. The results of the analysis are reported in Table 6.

TABLE 6

|  | WHSV ($h^{-1}$) | Conversion rate (%) | Selectivity (%) |
| --- | --- | --- | --- |
| Example 21 | 0.3 | 100.00 | 93.87 |
| Example 22 | 0.6 | 100.00 | 93.69 |
| Example 23 | 0.8 | 100.00 | 93.82 |
| Example 1 | 1.0 | 100.00 | 91.89 |
| Example 24 | 1.2 | 100.00 | 89.65 |
| Example 25 | 1.4 | 100.00 | 86.25 |
| Example 26 | 1.7 | 100.00 | 86.66 |
| Example 27 | 2.0 | 99.99 | 82.24 |

As shown in Table 6, when OPP is prepared by using the catalyst composition of the present disclosure, the suitable range of WHSVs was broader, such that high conversion rates are obtained for all of the reactions. Further, the selectivity of the product could be maintained under the condition of 99.99% of the conversion rate of the reactant. Also, the excellent catalytic activity of the catalyst composition of the present disclosure could be maintained under the condition of a broad range of WHSVs of the reactant.

In the method for preparing OPP of the present disclosure, the WHSV in the dehydrogenation reaction was between 0.3 and 2.0, and preferably between 0.3 and 1.4.

Moreover, in Example 21, by collecting the product and analyzing it with gas chromatography after a continuous reaction for 2400 hours, it is found that the conversion rate of the cyclohexanone dimer was still maintained at 100%. Further, the selectivity of OPP was 90.69%, under the condition of a conversion degree of the cyclohexanone dimer of 100%.

It can be seen that, after 2400 hours of reaction, the catalyst composition of the present disclosure resulted in a conversion rate maintained at 100%, and a selectivity of greater than 90%. Also, the catalytic activity was still high after 2400 hours of reaction.

From the above, as compared with the drawbacks in the prior art, the catalyst composition of the present disclosure employs a carrier that carries platinum, a metal selected from the first, second and third rows of transition metals of groups VIB and VIIIB, and a catalytic promoter at the same time, so as to effectively increase the dispersity of the active metal platinum on the catalyst and maintain a high conversion rate for a long time, and thereby increasing the catalytic activity.

Furthermore, by using a combination of the first active metal, the second active metal and the catalytic promoter with the specific amounts, and adjusting the amount of the catalytic promoter, the catalyst composition of the present disclosure can effectively decrease the acidity of the catalyst. When a dehydrogenation reaction is performed by using the catalyst composition of the present disclosure, the service life of the catalyst can be effectively and significantly increased, such that the catalyst composition of the present disclosure has a certain level of stability, and thereby being useful for industrial production.

Moreover, the method for preparing OPP of the present disclosure results in a broader range of the weight ratios of the reactant to the catalyst, such that it can be suitably applied in different fixed-bed reactors or different processing conditions. Thus, the method of the present disclosure exhibits a broad range of industrial applications.

The features and functions of the present disclosure have been elucidated in the foregoing detailed descriptions. Those skilled in the art will appreciate that modifications and variations according to the spirit and principle of the present disclosure may be made. All such modifications and variations are considered to fall within the spirit and scope of the present disclosure as defined by the appended claims.

What is claimed is:

1. A catalyst composition for preparing o-phenylphenol, comprising:
   a carrier; and
   a first active metal, a second active metal and a catalytic promoter carried by the carrier, wherein the first active metal is platinum, the second active metal is selected from the group consisting of chromium, ruthenium, and nickel, and the catalytic promoter is selected from the group consisting of alkali metal sulfate, alkali metal carbonate, alkali metal nitrate and alkali metal hydroxide, and wherein a weight ratio of the second active metal to the first active metal is between 0.03 and 0.38.

2. The catalyst composition for preparing o-phenylphenol according to claim 1, wherein a weight ratio of the first active metal to the carrier is between 0.004 and 0.006.

3. The catalyst composition for preparing o-phenylphenol according to claim 1, wherein a weight ratio of the second active metal to the carrier is between 0.0002 and 0.0015.

4. The catalyst composition for preparing o-phenylphenol according to claim 3, wherein the weight ratio of the second active metal to the carrier is between 0.0005 and 0.0012.

5. The catalyst composition for preparing o-phenylphenol according to claim 1, wherein the catalytic promoter is at least one selected from the group consisting of potassium sulfate and potassium carbonate.

6. The catalyst composition for preparing o-phenylphenol according to claim 1, wherein a weight ratio of the catalytic promoter to the carrier is between 0.02 and 0.15.

7. The catalyst composition for preparing o-phenylphenol according to claim 1, wherein the carrier is at least one selected from the group consisting of $SiO_2$, $Al_2O_3$, and $Zr_2O_3$.

8. A method for preparing o-phenylphenol, comprising:
performing a dehydrogenation reaction of a cyclohexanone dimer in the presence of the catalyst composition according to claim 1.

9. The method for preparing o-phenylphenol according to claim 8, wherein the weight hourly space velocity (WHSV) of the cyclohexanone dimer in the dehydrogenation reaction is between 0.2 and 2.0.

10. The method for preparing o-phenylphenol according to claim 8, wherein a weight ratio of the first active metal to the carrier is between 0.004 and 0.006.

11. The method for preparing o-phenylphenol according to claim 8, wherein a weight ratio of the second active metal to the carrier is between 0.0002 and 0.0015.

12. The method for preparing o-phenylphenol according to claim 8, wherein the metal salt is at least one selected from the group consisting of potassium sulfate and potassium carbonate.

13. The method for preparing o-phenylphenol according to claim 8, wherein the metal hydroxide is an alkali metal hydroxide.

14. The method for preparing o-phenylphenol according to claim 8, wherein a weight ratio of the catalytic promoter to the carrier is between 0.02 and 0.15.

15. The method for preparing o-phenylphenol according to claim 8, wherein the carrier is at least one selected from the group consisting of $SiO_2$, $Al_2O_3$, and $Zr_2O_3$.

* * * * *